United States Patent
Roehrig et al.

(10) Patent No.: US 6,198,838 B1
(45) Date of Patent: Mar. 6, 2001

(54) METHOD AND SYSTEM FOR DETECTION OF SUSPICIOUS LESIONS IN DIGITAL MAMMOGRAMS USING A COMBINATION OF SPICULATION AND DENSITY SIGNALS

(75) Inventors: Jimmy R. Roehrig; Takeshi Doi, both of Palo Alto, CA (US); Nico Karssemeijer, Beek; Guido M. Te Brake, Utrecht, both of (NL)

(73) Assignee: R2 Technology, Inc., Los Altos, CA (US)

( * ) Notice: Subject to any disclaimer, the term of this patent is extended or adjusted under 35 U.S.C. 154(b) by 0 days.

(21) Appl. No.: 09/141,289

(22) Filed: Aug. 27, 1998

Related U.S. Application Data (63) Continuation-in-part of application No. 09/103,290, filed on Jun. 23, 1998, which is a continuation of application No. 08/676,660, filed on Jul. 10, 1996, now Pat. No. 5,815,591.

(51) Int. Cl.$^7$ ..................................................... G06K 9/00
(52) U.S. Cl. .............................................. 382/132; 378/37
(58) Field of Search ..................................... 382/128–133, 382/156, 159, 181, 190, 191, 195, 203, 224, 227, 291, 308; 378/37, 62, 63, 98.11; 600/410, 425, 408; 128/915

(56) References Cited

U.S. PATENT DOCUMENTS

| | | | |
|---|---|---|---|
| 5,003,979 | * 4/1991 | Merickel et al. | 600/410 |
| 5,133,020 | * 7/1992 | Giger et al. | 382/128 |
| 5,260,871 | * 11/1993 | Goldberg | 600/320 |
| 5,586,160 | * 12/1996 | Mascio | 378/37 |
| 5,622,171 | * 4/1997 | Asada et al. | 600/408 |
| 5,627,907 | * 5/1997 | Gur et al. | 382/132 |
| 5,657,362 | * 8/1997 | Giger et al. | 378/37 |
| 5,673,332 | * 9/1997 | Nishikawa et al. | 382/128 |
| 5,799,100 | * 8/1998 | Clarke et al. | 382/132 |
| 5,828,774 | * 10/1998 | Wang | 382/128 |
| 5,832,103 | * 11/1998 | Giger et al. | 382/130 |
| 5,854,851 | * 12/1998 | Bamberger et al. | 382/132 |

OTHER PUBLICATIONS

Baker et al., 1996, "Artificial Neural Network: Improving the Quality of Breast Biopsy Recommendations," *Radiology* 198:131–135.

Bick et al., 1995, "A New Single–Image Method for Computer–Aided Detection of Small Mammographic Masses," In: Computer Assisted Radiology: Proceedings of the International Symposium on Computer and Communication Systems for Image Guided Diagnosis and Therapy, Lemke et al., eds. CAR '95 Berlin, Jun. 21–24, 1995.

Brzakovic et al., 1993, "An approach to automated screening of mammograms," *SPIE* 1905:690–701.

Crooks and Fallone, 1993, "A novel algorithm for the edge detection and edge enhancement of medical images," *Med. Phys.* 20(4):993–998.

(List continued on next page.)

*Primary Examiner*—Jayanti K. Patel
(74) *Attorney, Agent, or Firm*—Pennie & Edmonds LLP (57) ABSTRACT

A method and system for detecting suspicious portions of digital mammograms by using independently calculated mass and spiculation information is disclosed. The method is for use in a computer aided diagnosis system that is designed to bring suspicious or possibly cancerous lesions in fibrous breast tissue to the attention of a radiologist or other medical professional. In a preferred embodiment, spiculation information and mass information are independently calculated, with the computed spiculation information not being dependent on results of the mass information computation, thus leading to greater reliability. Systems according to a preferred embodiment also compute spiculation information either prior to, or concurrently with, the computation of mass information, thus allowing increased overall system speed.

20 Claims, 4 Drawing Sheets

OTHER PUBLICATIONS

Doi et al., 1995, "Potential Usefulness of Digital Imaging in Clinical Diagnostic Radiology: Computer–Aided Diagnosis," *Journal of Digital Imaging* 8(1):2–7.

Feig and Yaffe, 1995, "Digital Mammography, Computer–Aided Diagnosis, and Telemammography," *The Radiologic Clinics of North America: Breast Imaging* 33(6)6: 1205–1230.

Floyd et al., 1994, "Prediction of Breast Cancer Malignancy Using an Artificial Neural Network," *Cancer* 74(11):2944–2948.

Giger et al., 1993, "An 'Intelligent' Workstation for Computer–aided Diagnosis," *Radiographics* 13(3):647–656.

Groshong and Kegelmeyer, 1996, "Evaluation of a Hough Transform Method for Circumscribed Lesion Detection," In: *Digital Mammography '96*, Doi et al., eds. Elsevier Science B.V. pp. 361–366.

Gurney, 1994, "Neural Networks at the Crossroads: Caution Ahead," *Radiology* 193:27–30.

Huo, et al., 1995, "Analysis of spiculation in the computertized classification of mammographic masses," *Med. Phys.* 22 (10): 1569–1579.

Karssemeijer, 1994, "Recognition of stellate lesions in digital mammograms,"In: *Digital Mammography*, Gale et al., eds., pp. 211–219.

Karssemeijer, 1995, "Detection of stellate distortions in mammograms using scale space operators," In: *Information Processing in Medical Imaging*, Bizais et al., eds. Kluwer Academic Publishers, Netherlands, pp. 335–346.

Katsuragawa, 1990, "Image feature analysis and computer–aided diagnosis in digital radiography: Effect of digital parameters on the accuracy of computerized analysis of interstitial disease in digital chest radiographs," *Med. Phys.* 17(1):72–78.

Kegelmeyer et al., 1993, "Evaluation of stellate lesion detection in a standard mammogram data set," *SPIE* 1905:787–798.

Kegelmeyer et al., 1994, "Computer–aided Mammographic Screening for Spiculated Lesions," *Radiology* 191:331–337.

Lin et al., "Application of Neural Networks for Improvement of Lung Nodule Detection in Digital Chest Radiographs," pp. IV–20⁻–IV–23.

Nishikawa et al., "Computer–aided Detection and Diagnosis of Masses and Clustered Microcalcifications from Digital Mammograms," In: *State of the Art in Digital Mammographic Image Analysis*, Bowyer and Astley, eds. World Scientific Publishing Co., 1993.

Sahineret al., 1996, "Classification of masses on mammograms using rubber–band straightening transform and feature analysis," *SPIE* 2710:44–50.

Schmidt et al., "Computer–aided Diagnosis in Mammography," *RSNA Categorical Course in Breast Imaging 1995*; pp. 199–208.

Specht, 1990, "Probabilistic Neural Networks," *Neural Networks* 3:109–118.

Specht, "Enhancements to Probabilistic Neural Networks," Proceedings of the IEEE International Joint Conference on Neural Networks, Baltimore, MD. Jun. 7–11, 1992.

Specht and Romsdahl, "Experience with Adaptive Probabilistic Neural networks and Adaptive General Regression Neural Networks," IEEE International Conference on Neural Networks, Orlando, Florida. Jun. 28 to Jul. 2, 1994.

Tahoces et al., 1995, "Computer–assisted diagnosis: the classification of mammographic breast parenchymal patterns," *Phys. Med. Biol.* 40:103–117.

te Brake and Karssemeijer, 1996, "Detection of Stellate Breast Abnormalities," In: *Digital Mammography '96*, Doi et al., eds. Elsevier Science B. V. pp. 341–346.

Thurfjell et al., 1998, "Sensitivity and Specificity of Computer–Assisted Breast Cancer Detection in Mammography Screening," *Acta Radiologica* 39: 384–388.

Vyborny and Giger, 1994, "Computer Vision and Artificial Intelligence in Mammography," *AJR* 162:699–708.

Wei et al., 1995, "Classification of mass and normal breast tissue on digital mammograms: Multiresolution texture analysis," *Med. Phys.* 22(9):1501–1513.

Wu et al., 1993, "Artificial Neural Networks in Mammography: Application to Decision Making in the Diagnosis of Breast Cancer," *Radiology* 187: 81–87.

Yin et al., 1991, "Computerized detection of masses in digital mammograms: Analysis of bilateral subtraction images," *Med. Phys.* 18(5):955–963.

Yoshimura et al., 1992, "Computerized Scheme for the Detection of Pulmonary Nodules: A Nonlinear Filtering Technique," *Invest. Radiol.* 27:124–129.

Zhang and Giger, 1995, "Automated detection of spiculated lesions and architectural distortions of digitized mammograms," *SPIE* 2434:846–854.

Zheng et al., 1995, "Computerized Detection of Masses in Digitized Mammograms Using Single–Image Segmentation and a Multilayer Topographic Feature Analysis," *Acad. Radiol.* 2:959–966.

* cited by examiner

METHOD AND SYSTEM FOR DETECTION OF SUSPICIOUS LESIONS IN DIGITAL MAMMOGRAMS USING A COMBINATION OF SPICULATION AND DENSITY SIGNALS

CROSS-REFERENCE TO RELATED APPLICATIONS

This application is a continuation-in-part of U.S. patent application Ser. No. 09/103,290, entitled "Method and Apparatus for Fast Detection of Spiculated Lesions in Digital Mammograms," filed Jun. 23, 1998, which is a continuation of U.S. patent application Ser. No. 08/676,660, now U.S. Pat. No. 5,815,591 issued Sep. 29, 1998. Both of the above applications are assigned to the assignee of the present invention. The above applications are hereby incorporated by reference into the present application.

FIELD OF THE INVENTION

The present invention relates to the field of computer aided diagnosis of medical images. In particular, the invention relates to a method and apparatus for detecting suspicious lesions in digital mammograms using an algorithm that independently computes mass information and spiculation information for allowing faster and more reliable identification of suspicious lesions.

BACKGROUND OF THE INVENTION

Breast cancer in women is a serious health problem. The American Cancer Society currently estimates that over 180,000 U.S. women are diagnosed with breast cancer each year. Breast cancer is the second major cause of cancer death among women. The American Cancer Society also estimates that breast cancer causes the death of over 44,000 U.S. women each year. While, at present, there is no means for preventing breast cancer, early detection of the disease prolongs life expectancy and decreases the likelihood of the need for a total mastectomy. Mammography using x-rays is currently the most common method of detecting and analyzing breast tumors.

Detection of suspicious, i.e. possibly cancerous, areas in mammograms is an important first step in the early diagnosis and treatment of breast cancer. While it is important to detect suspicious lesions when they are in the early stages, practical considerations can make this difficult. One complicating factor is that a typical mammogram may contain myriads of lines corresponding to fibrous breast tissue. The trained, focused eye of a medical professional, such as a radiologist, is needed to detect suspicious features among these lines. A typical radiologist may be required to examine hundreds of mammograms per day, leading to the possibility of a missed diagnosis due to fatigue and human error.

Recently, medical professionals have begun to use Computer Aided Diagnostic (CAD) tools to assist them in detecting suspicious features. Experiments have shown that the performance of radiologists improve when they are assisted by detection software that marks suspicious areas. See Brake and Karssemeijer, "Detection of Stellate Breast Abnormalities," *Digital Mammography* pp. 341–346 (Elsevier Science 1996), the contents of which are hereby incorporated by reference into the present disclosure.

Figure 1:
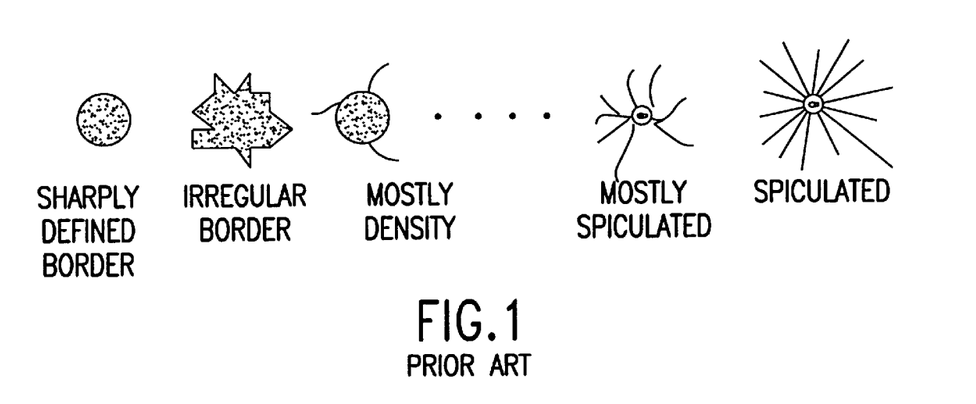
FIG. 1 shows various types of lesions arranged in an order from pure mass to highly spiculated mass.

FIG. 1 shows a continuum of lesions that may appear in mammograms, ranging from a pure mass or pure density lesion on the left to a spiculated lesion on the right. Other types of lesions include architectural distortions, which have radiating lines similar to spiculated lesions but are generally without a central mass, and radial scars, which appear as criss-crossed lines and also are generally without a central mass.

Sharply defined masses such as those shown at the left in FIG. 1 are rarely associated with malignant tumors, while spiculated masses can be a strong indication of malignancy. Lesions having the characteristics of architectural distortions or radial scars may also be cancerous, depending on their size and shape.

Accordingly, there is value in locating and analyzing both the "mass" or "density" qualities and the "spiculatedness" qualities of shapes found in digital mammograms. CAD systems generally include "mass" (or density) focused algorithms and "spiculation" focused algorithms. Some algorithms attempt to use metrics of both "massness" and "spiculatedness" to identify suspicious portions of digital mammograms. Such algorithms are included among the following references: Yin and Giger et. al., "Computerized Detection of Masses in Digital Mammograms: Analysis of Bilateral Subtraction Images," *Medical Physics*, Vol. 18, No. 5, pp. 955–963 (Sept./Oct. 1991); Sahiner et. al., "Classification of Masses on Mammograms Using a RubberBand Straightening Transform and Feature Analysis," *Medical Imaging, SPIE Symposium on Medical Imaging* Paper No. 2710-06, at p. 204 (1996); and Huo and Giger et al., "Analysis of Spiculation in the Computerized Classification of Mammographic Masses," *Medical Physics*, Vol. 22, No. 10, pp. 1569–1579 (Oct. 1995). The contents of the above references are hereby incorporated by reference into the present application.

Typical of the above algorithms, Huo and Giger take a serial and dependent approach by first identifying masses and subsequently identifying spiculatedness characteristics of those masses. Huo and Giger demonstrate how the edges of detected masses can be used to determine a measure of spiculation—i.e., spiculatedness. Huo and Giger, approach the problem serially by first detecting the mass signature, or density, in a mammogram, and then applying various filtering analyses to filter out benign masses and false detections, such as parenchymal structure. The Huo and Giger approach initially depends on density, which is a feature with low positive predictive value. It then attempts to improve upon itself by measuring features with higher positive predictive values, such as spiculation. The shortcomings of the Huo/Giger approach include the fact that the additional feature measurements typically depend on secondary algorithms that may be non-robust. These secondary algorithms may include algorithms for spiculation, region growing, or segmentation of the mass boundaries. Also, these algorithms may display poor sensitivity on architectural distortions and radial scars which have no central density. Finally, because the algorithm is inherently serial, wherein the spiculation information is computed after the mass information, the time for completion of the algorithm is the sum of the time for completion of the mass detection algorithm plus the spiculation detection algorithm, which can lead to disadvantageously slow results.

A direct "backward direction" algorithm for of spiculation detection is disclosed in Karssemeijer, "Recognition of Stellate Lesions in Digital Mammograms," *Digital Mammography: Proceedings of the 2nd International Workshop on Digital Mammography*, York, England, Jul. 10–12, 1994, pp. 211–219 (Elsevier Science 1994), the contents of which are hereby incorporated by reference into the present application. By "backward direction" it is meant that a "candidate point" is incrementally moved across the image by a distance corresponding to the desired resolution of the spiculation search. At each candidate point, a set of "window computations" for a window of pixels surrounding the candidate point is performed, and a metric corresponding to the presence and/or strength of a spiculation centered on the candidate point is computed.

"Backward direction" algorithms are computationally intensive. For an image size of N×N pixels, there generally need to be on the order of $K(bN)^2$ computations, where K is the number of window computations for each candidate point and b is the reciprocal of the number of image pixels between each candidate point. Because the number K is often proportional to the square or cube of the window size, the computational intensity of "backward direction" approaches can easily become unwieldy. Another example of a "backward direction" spiculation algorithm is described in Kegelmeyer, "Computer-aided Mammographic Screening for Spiculated Lesions," *Radioloqy*, Vol. 191, pp. 331–337 (1994), the contents of which are hereby incorporated by reference into the present application. The computational complexity of "backward direction" spiculation algorithms may cause a CAD program to be too slow for practical use by medical professionals, such as radiologists. Additionally, a practical implementation of a CAD system using a backward direction algorithm for spiculation detection would lead to inevitable dependency between the mass and spiculation algorithms. This is because, due to its slowness, the spiculation algorithm could only be applied to a subset of interesting regions of the digital mammogram image, the interesting regions being pointed out by the presence of masses from the mass detection algorithm.

Accordingly, it would be desirable to provide a computer-assisted diagnosis (CAD) system for assisting in the detection of suspicious lesions in medical images that has increased speed in computing the necessary mass information and spiculation information.

It would be further desirable to provide a computerassisted diagnosis (CAD) system that has greater reliability in detecting suspicious lesions of a digital mammogram that have characteristics similar to those of architectural distortions, radial scars, and spiculated lesions having very small central masses.

SUMMARY OF THE INVENTION

These and other objects of the present invention are achieved by an improved CAD system that incorporates independent measurements of mass and spiculation characteristics as taken from a digital mammogram image. In a preferred embodiment, a forward spiculation detection algorithm is incorporated that is executed separately from a mass detection algorithm, and that is not dependent on any results from the mass detection algorithm. The step of computing spiculation information may be performed before, during, or after the step of computing mass information, but in a preferred embodiment is performed concurrently in time with the mass detection algorithm for optimal time performance of the overall system.

According to a preferred embodiment, after the mass information and spiculation information is determined, a classifier algorithm classifies locations in the digital mammogram according to their feature vectors, which comprise the computed mass information and spiculation information. The classifier algorithm may incorporate any of a variety of classification algorithms known in the art, including linear classifier algorithms, quadratic classifier algorithms, K-nearest-neighbor classifier algorithms, decision tree classifier algorithms, or neural network classifier algorithms. By way of non-limiting example, the classifier algorithm may classify locations into a two-category system including a "suspicious" category and a "normal" category.

BRIEF DESCRIPTION OF THE DRAWINGS

These and other objects, features and advantages of the present invention will be more readily apparent from the following detailed description of the invention in which.

DETAILED DESCRIPTION OF THE INVENTION

Figure 2A:
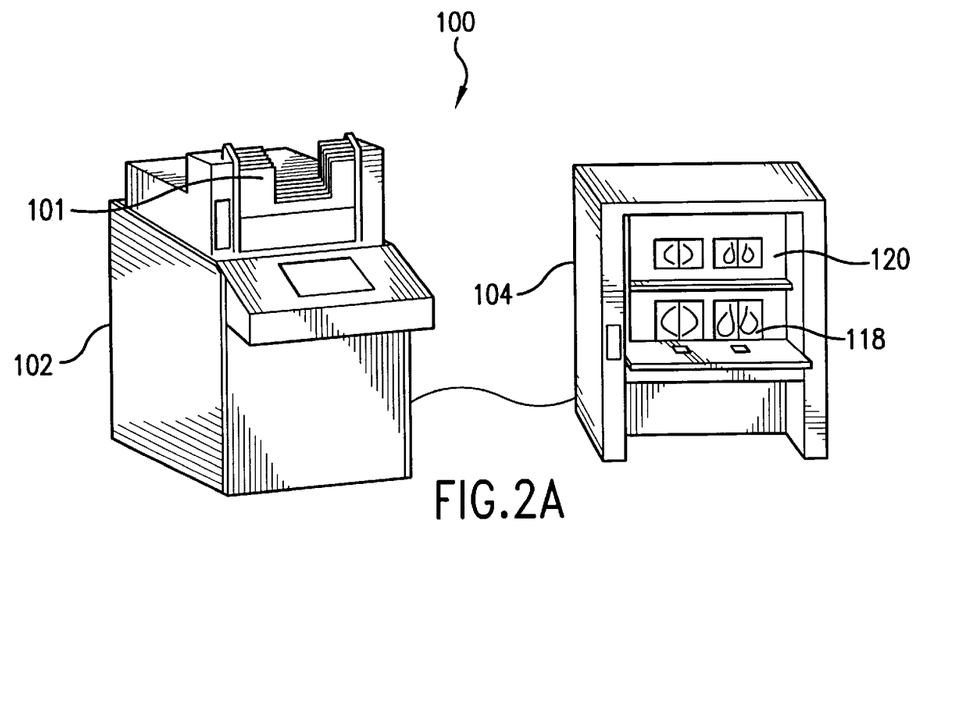
FIG. 2A is an outside view of an illustrative computer aided diagnostic (CAD) system.

FIG. 2A is an outside view of an illustrative computer aided diagnostic (CAD) system 100 for assisting in the identification of suspicious areas in mammograms according to the preferred embodiment. CAD system 100 comprises a CAD processing unit 102 and a viewing station 104. In general, CAD processing unit 102 scans a developed x-ray mammogram 101 into a digital mammogram image, processes the image, and outputs a highlighted digital mammogram for viewing at viewing station 104.

Figure 2B:
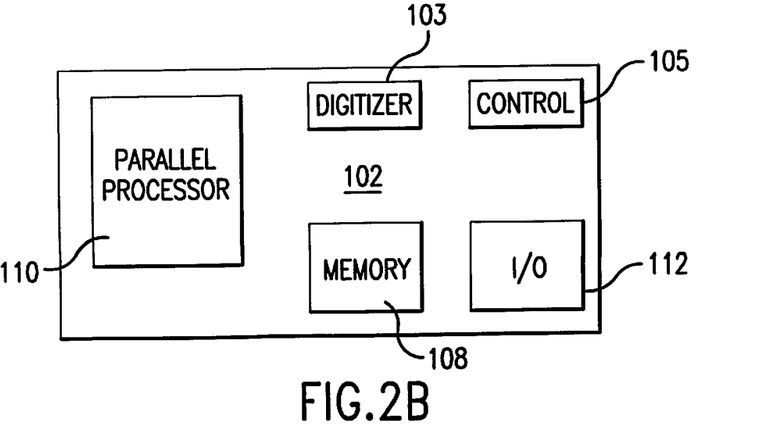
FIG. 2B is a block diagram of an illustrative CAD processing unit for use in the CAD system of FIG. 2A.

FIG. 2B is a block diagram of CAD processing unit 102. In accordance with the invention, processing unit 102 is capable of performing a multiplicity of image processing algorithms designed to detect abnormalities such as spiculation detection, mass detection, linear weighted comparisons and general mathematical comparisons, either serially or in parallel with the disclosed abnormality detection algorithms. Preferably, CAD processing unit 102 includes a digitizer 103, a central control unit 105, a memory 108, a parallel processing unit 110, and I/O unit 112. Digitizer 103 illustratively is a scanner with 50 micron resolution.

Viewing station 104 is for conveniently viewing both the x-ray mammogram 101 on a backlighting station 120 and the output of the CAD processing unit 102 on a display device 118. The display device 118 may be, for example, a CRT screen. The display device 118 typically shows a highlighted digital mammogram corresponding to the x-ray mammogram 101, the highlighted digital mammogram having information directing the attention of the radiologist to suspicious areas which may contain spiculation as determined by image processing steps performed by the CAD processing unit 102. In one embodiment of the invention, the highlighted digital mammogram will have black or red circles circumscribing locations with suspected abnormalities. Since the x-ray mammogram 101 on backlighting station 120 and the digitized mammogram on display device 118 are physically adjacent one another, one application of viewing station 104 is to use the digitized mammogram to direct the attention of the radiologist to the spiculated portions of the actual x-ray mammogram 101 itself.

It is to be appreciated that the CAD processing unit 102 is capable of performing other image processing algorithms on the digital mammogram in addition to or in parallel with the algorithms for detecting abnormalities in accordance with the preferred embodiment. In this manner, the radiologist may be informed of several suspicious areas of the mammogram at once by viewing the display device 118, spiculation being one special type of suspicious area.

After the x-ray mammogram 101 passes through the CAD system 100, it undergoes processing similar to that currently practiced in clinics. In addition, memory 108 of CAD processing unit 102 may be used in conjunction with I/O unit 112 to generate a permanent record of the highlighted digital mammogram described above, and/or may also be used to allow non-real-time viewing of the highlighted digital mammogram.

Figure 3:
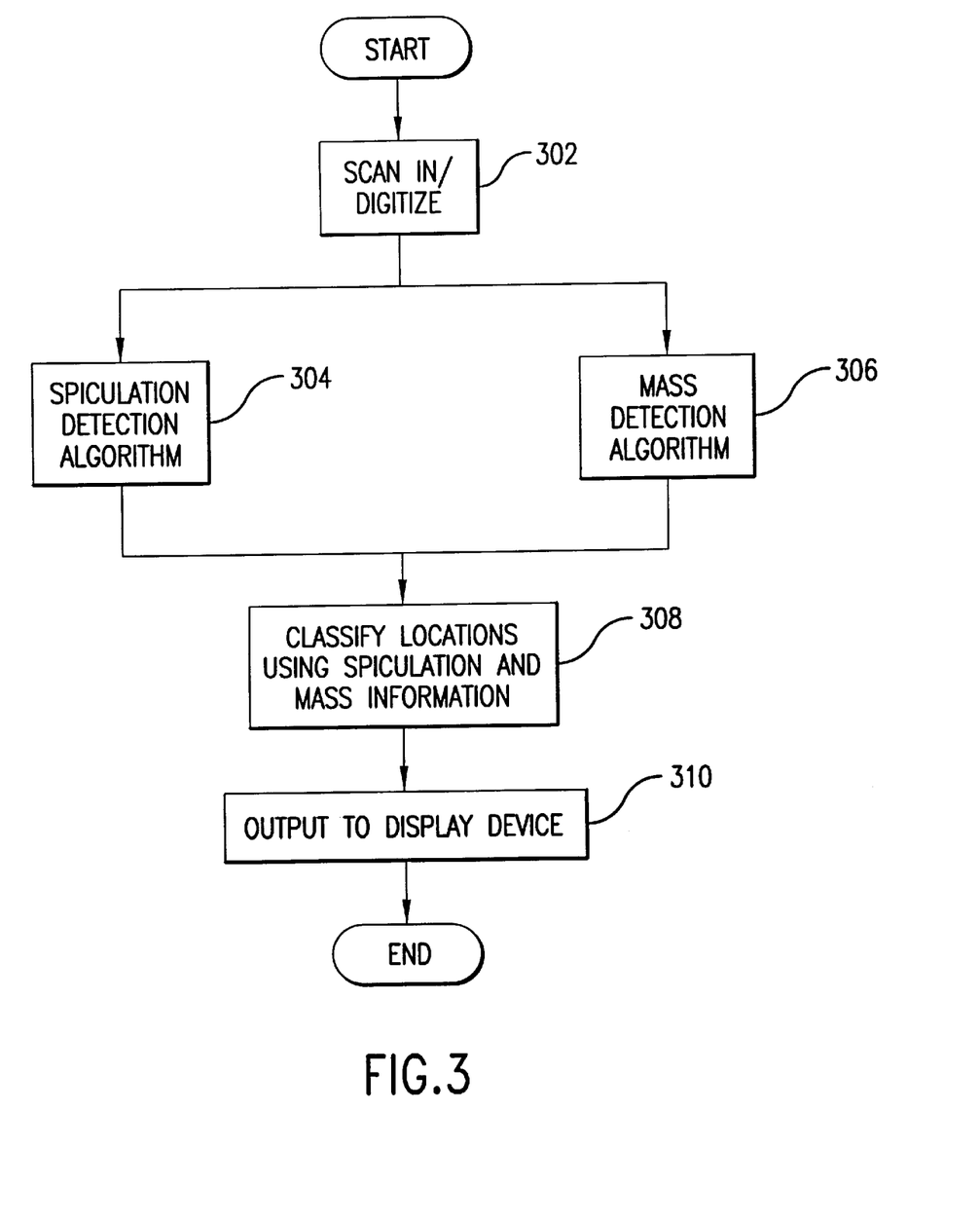
FIG. 3 is a flowchart showing steps taken by a CAD system in accordance with a preferred embodiment.

FIG. 3 is an overview showing steps performed by CAD processing unit 102 on the x-ray mammogram in accordance with a preferred embodiment. At step 302, the x-ray mammogram is scanned in and digitized into a digital mammogram. The digital mammogram may be, for example, a 3000×4000 array of 12-bit gray scale pixel values. Such a digital mammogram would generally correspond to a typical 8"×10" x-ray mammogram which has been digitized at a 50 micron spatial resolution. Because a full resolution image such as the 3000×4000 image described above is not necessary for the effectiveness of the preferred embodiment, the image may be locally averaged, using steps known in the art, down to a smaller size corresponding, for example, to a 200 micron spatial resolution. At such a resolution, a typical image would then be an M×N array of 12-bit gray scale pixel values, with M being near 900, for example, and N being near 1200, for example. In general, however, either the full resolution image or the locally averaged image may be used as the original digital mammogram in accordance with the preferred embodiment.

At step 304, a spiculation detection algorithm is performed on the digital mammogram. At step 306 a mass detection algorithm is run on the digital mammogram. In a preferred embodiment, steps 304 and 306 are carried out concurrently so as to optimize overall speed of the detection process. Also in a preferred embodiment, steps 304 and 306 are carried out independently, in that there is no data dependence between them. According to a preferred embodiment, the spiculation detection step 304 does not require any final or intermediate outputs from the mass detection step 306, and the mass detection step 306 does not require any final or intermediate outputs from the spiculation detection step 304. In addition to introducing the ability to make the overall algorithm faster, the independence of the mass detection and spiculation detection steps allows for increased detection of features characteristic of architectural distortions, radial scars, and in general otherwise suspicious lesions that do not have a significant central mass that is detected by the mass detection algorithm.

At step 308, a classifier algorithm is performed on feature vectors corresponding to locations in the digital mammogram. Each location in the digital mammogram has a corresponding feature vector, which can be defined as a set of characteristics, including the "massness" metrics and "spiculatedness" metrics that were determined previously at steps 304 and 306. A classifier is an algorithm or system that labels a feature vector as belonging to a specific class, such as "suspicious/normal," "malignant/benign," etc. Several types of classifiers exist in the art, including linear classifiers, quadratic classifiers, k-nearest-neighbor method classifiers, decision trees, and neural networks. As known in the art, classifiers are constructed using a data set of example vectors representing each class, called a training set or learning set. See generally Brake & Karssemeijer, supra, and references cited therein. Finally, at step 312, the digital mammogram image and a list of suspicious lesions are sent to the viewing station 104 for display.

Many spiculation detection algorithms are known in the art. Any number of these spiculation detection algorithms may be used to accomplish step 304. For example, step 304 may be satisfied by running either a backward or a forward spiculation detection algorithm. However, backward spiculation detection algorithms consume substantially more time, computer memory, and general resources than forward spiculation detection algorithms. For this reason, a preferred embodiment uses a forward spiculation detection algorithm. The information resulting from a spiculation detection algorithm may include such details as the geometrical coordinates of mammographic areas likely to contain spiculations, the size of the spiculation, or the like.

In step 306 of FIG. 3, a mass detection algorithm is run against the digitized mammogram. Importantly, step 306 is independent of step 304 in that the mass detection algorithm is run against the digitized mammogram without reference to the spiculation detection algorithm of step 304, or the results of the spiculation detection algorithm of step 304. The independent nature of steps 304 and 306 is important because it solves the problem of that prior art in which a mass detection algorithm and a spiculation detection algorithm are serially applied. In the prior art, a mass detection algorithm is applied to the digitized image first so that areas with "density," or mass, can be identified. In this way, a mass detection algorithm making a "first cut" singles out only areas that may contain suspicious masses. Next, a spiculation detection algorithm is applied only to those suspicious areas that may contain masses, rather than to the entire mammographic image. Thus, spiculated masses with low density may be overlooked.

The preferred embodiment solves the "first cut" problem of the prior art because both a spiculation detection algorithm, step 304, and a mass detection algorithm, step 306, are independently applied to the entire mammographic image. By applying both a spiculation detection algorithm and a mass detection algorithm to the entire image, an increased number of suspicious areas are likely to be identified. For example, areas containing low density spiculated masses may be identified. Step 306 can be executed using any number of mass detection algorithms known in the art.

Figure 4:
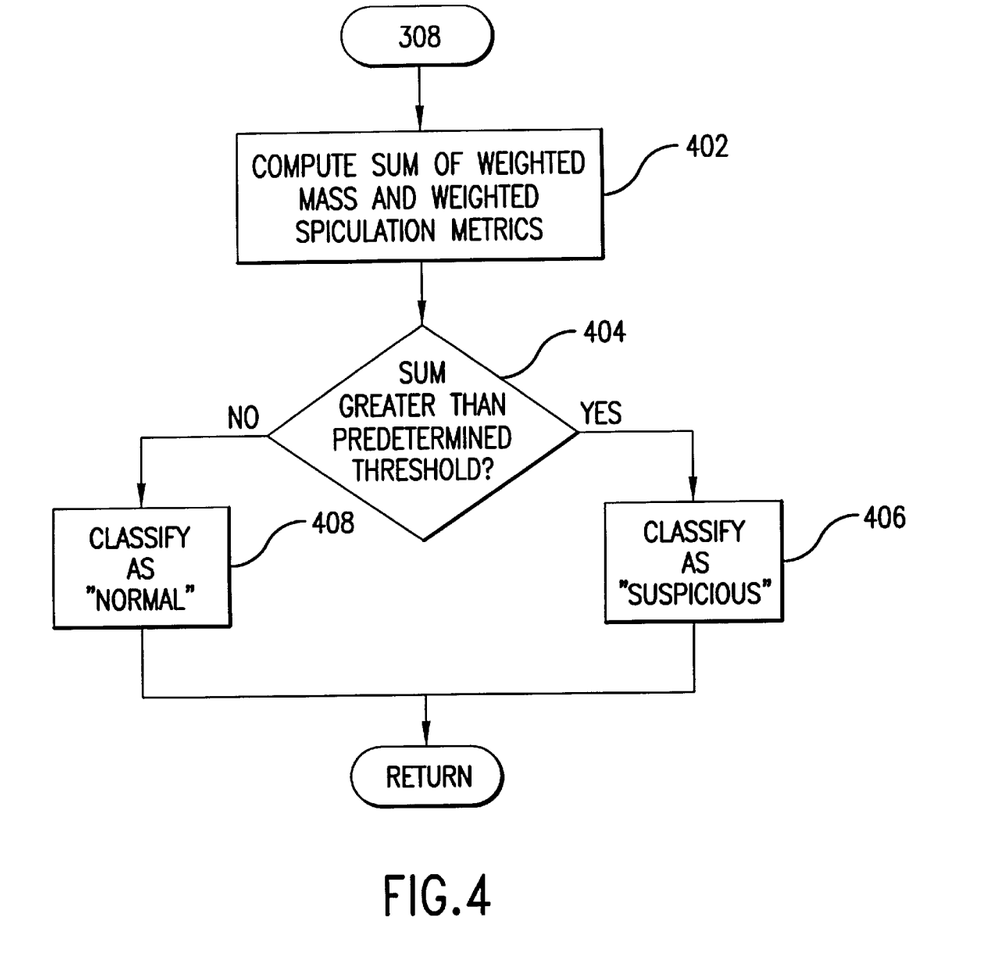
FIG. 4 is a flowchart showing further steps taken by a CAD system in accordance with a preferred embodiment.

FIG. 4 shows exemplary steps corresponding to the classification step 308 when a simple linear classifier method is used. The example of FIG. 4 is presented for clarity and completeness of disclosure, to allow the reader to more fully comprehend the context of the preferred embodiment, and is not intended to limit the scope of the present invention. It is to be understood that any of a variety of classifiers can be used at step 308, each having certain advantages, disadvantages, and tradeoffs in terms of training time, computation time, probability of false positives, probability of missed detection, and other factors. The method described herein has an advantage, however, of simplicity and speed of training and computation time.

The classification method of FIG. 4 supposes the common result that the spiculation detection algorithm and the mass detection algorithm produce a scalar spiculation metric $f_s$ and a scalar mass metric $f_m$, respectively, each having a value normalized between 0 and 100, for example. Thus, for example, a given location may have a scalar spiculation metric $f_s$ of 90, which would indicate a very high degree of spiculatedness, and a scalar mass metric $f_m$ of 5, which would indicate a very faint or small mass. In this simple case, the pair $(f_s, f_m)$ forms the feature vector at each location.

At step 402, the scalar spiculation metric $f_s$ and the scalar mass metric $f_m$ are each multiplied by weighting factors $a_s$ and $a_m$, respectively, and the weighted factors are added to form a result. At step 404, the result from step 402 is compared to a predetermined threshold C. If the result from step 402 is greater than the predetermined threshold C, the location is identified as "suspicious" at step 406. Otherwise, the location is identified as "normal" at step 408. The choices for $a_s$, $a_m$, and C define the parameters for the linear classifier algorithm of FIG. 4. Using methods known in the art, these linear classifier parameters are statistically preselected using a large training set of feature vectors that are known to represent each class being identified.

As known in the art, the parameters of the classifier may be changed to achieve different levels of utility and results. Even in the simple linear classifier example of FIG. 4, it is readily observed that the predetermined threshold C may be lowered to increase system sensitivity and bring more mammograms to the attention of the radiologist. This would, of course, have the negative impact of increasing the overall number of mammograms and false positives that the radiologist must analyze. Conversely, the predetermined threshold C may be increased to decrease system sensitivity, and would have the converse result of necessitating less radiologist intervention while risking more missed diagnoses.

The linear classifier technique of FIG. 4 can be generalized and extended to include several feature vector metrics (f1, f2, f3, . . . ) and several weights (a1, a2, a3 . . . ). Other feature vector metrics may include, for example, the "sphericity" and "eccentricity" metrics disclosed in the parent U.S. App. Ser. No. 09/103,290, supra.

It is also within the scope of the preferred embodiments to for the classifier to identify more than two classes. For example, a classifier may be constructed to form four sets—"suspicious —more spiculated"; "suspicious—more density;" "suspicious—similar density and spiculation", and "normal." One use of the multiple classes would be, for example, to place red triangles around "suspicious—more density" locations on the CRT display 118, placing blue triangles around "suspicious—more spiculation" locations, and green squares around "suspicious—similar density and spiculation" locations. In this manner, the radiologist would be made aware of different types of suspicious lesions in different ways.

An alternative embodiment uses a look up table to combine the independent information at each location in the digitized mammogram. The look up table might be a two dimensional matrix that indicates for numerical values of mass information on a first axis and spiculation information on a second axis whether the combination of mass information and spiculation information is suspicious.

Both linear classifiers and neural networks are types of classifiers. In order to be able to use a classifier, prior statistical knowledge about the digital mammograms is necessary. For example, see Brake and Karssemeijer, "Detection of Stellate Breast Abnormalities," *Digital Mammography* pp. 341–346 (Elsevier Science 1996). Other types of classifiers include the Bayes optimal classifier, quadratic classifiers, the kth-nearest neighbor classifier, and artificial neural networks, or the like. One skilled in the art will know that any of these pattern classification systems could be used according to the preferred embodiments.

Once an abnormality is located, the preferred embodiment could be extended to advantageously create further classification parameters to indicate areas according to probable seriousness or likelihood of locating a benign abnormality versus locating a malignant abnormality. Such a further classification step could assist the medical professional in decision making and prioritization.

Although preferred embodiments have been described with respect to a CAD system for detecting suspicious lesions in digital mammograms, those skilled in the art should be able to apply the preferred embodiments to any number of other computer aided diagnosis systems.

What is claimed is:

1. A method for automated detection of suspicious lesions in a digital mammogram, comprising the steps of:

computing mass information corresponding to the digital mammogram, said mass information having mass location information;

independent of said step of computing mass information, computing spiculation information corresponding to the digital mammogram, said spiculation information having spiculation location information; and identifying suspicious lesions in the digital mammogram using said mass information and said spiculation information.

2. The method of claim 1, wherein said step of computing spiculation information is performed prior to or concurrently with said step of computing mass information.

3. The method of claim 2, wherein said spiculation information is computed from a set of information other than said mass information, for allowing faster and more reliable detection of suspicious lesions in the digital mammogram.

4. The method of claim 3, wherein said step of identifying suspicious lesions includes the step of using a classifier algorithm to classify a feature vector corresponding to at least one location in said digital mammogram, each feature vector comprising that portion of said mass information and said spiculation information that corresponds to that location.

5. The method of claim 4, wherein said classifier algorithm is used to classify feature vectors associated with each location in said digital mammogram.

6. The method of claim 4, wherein said classifier algorithm comprises a linear classifier algorithm.

7. The method of claim 4, wherein said classifier comprises a quadratic classifier algorithm.

8. The method of claim 6, said mass information comprising a mass metric, said spiculation information comprising a spiculation metric, said mass metric and said spiculation metric being scalar quantities, said linear classifier algorithm comprising the steps of:

weighting said mass metric by a first weight to produce a weighted mass metric;

weighting said spiculation metric by a second weight to produce a weighted spiculation metric;

combining said weighted mass metric and said weighted spiculation metric to produce a result;

comparing said result to a predetermined threshold;

identifying the corresponding location as suspicious if said result is greater than said predetermined threshold; and identifying the corresponding location as normal if said result is not greater than said predetermined threshold.

9. The method of claim 8, wherein said first weight, said second weight, and said predetermined threshold are determined using a training algorithm on a training set of digital mammograms, said training set comprising a plurality of examples of suspicious lesions and a plurality of examples of normal breast structure.

10. A computer program product for directing a computing apparatus to automatically detect suspicious lesions in a digital mammogram, thus permitting the suspicious lesions to be brought to the attention of a medical professional, said computer program product comprising:

computer code for computing mass information corresponding to the digital mammogram, said mass information having mass location information;

computer code for computing, independent of the computation of said mass information, spiculation information corresponding to the digital mammogram, said spiculation information having spiculation location information; and computer code for identifying suspicious lesions in the digital mammogram using said mass information and said spiculation information.

11. The computer program product of claim 10, wherein said spiculation information is computed prior to or concurrently with said step of computing mass information.

12. The computer program product of claim 11, wherein said computer code for identifying suspicious lesions includes computer code for using a classifier algorithm to classify a feature vector corresponding to at least one location in said digital mammogram, each feature vector comprising that portion of said mass information and said spiculation information that corresponds to that location.

13. The computer program product of claim 12, wherein said classifier algorithm is used to classify feature vectors associated with each location in said digital mammogram.

14. The computer program product of claim 13, said mass information comprising a mass metric, said spiculation information comprising a spiculation metric, said mass metric and said spiculation metric being scalar quantities, said linear classifier algorithm comprising the steps of:

weighting said mass metric by a first weight to produce a weighted mass metric;

weighting said spiculation metric by a second weight to produce a weighted spiculation metric; combining said weighted mass metric and said weighted spiculation metric to produce a result;

comparing said result to a predetermined threshold;

identifying the corresponding location as suspicious if said result is greater than said predetermined threshold; and identifying the corresponding location as normal if said result is not greater than said predetermined threshold.

15. An automated system for detecting suspicious portions of a digitized mammogram, comprising:

means for computing mass information corresponding to the digitized mammogram, said mass information having mass location information;

means for computing spiculation information corresponding to the digitized mammogram independent of said mass information, said spiculation information having spiculation location information; and means for classifying said mass information and said spiculation information for detecting the suspicious portions of the digital mammogram.

16. The automated system of claim 15, wherein said means for computing spiculation information computes said spiculation information prior to or substantially in parallel with a period in which said means for computing mass information computes said mass information.

17. The automated system of claim 16, wherein said means for computing spiculation information computes said spiculation information using data other than said mass information.

18. The automated system of claim 17, wherein said means for classifying comprises:

means for computing at least one combined classification parameter defined by a combination of said mass information and said spiculation information; and means for identifying values for which said at least one combined classification parameter corresponds to a suspicious portion of the digital mammogram.

19. The automated system of claim 17, wherein said means for classifying comprises means for implementing a neural network algorithm capable of identifying the suspicious portions of the digital mammogram using said mass information and said spiculation information.

20. The automated system of claim 18, wherein said means for classifying includes a look up table that is indexed according to scalar quantities associated with said mass information and said spiculation information.

* * * * *